US009057090B2

(12) United States Patent
Kato et al.

(10) Patent No.: US 9,057,090 B2
(45) Date of Patent: *Jun. 16, 2015

(54) METHOD OF IDENTIFYING AN AGENT FOR INHIBITING ODOR OF PYRAZINE DERIVATIVES

(71) Applicant: Kao Corporation, Tokyo (JP)

(72) Inventors: Aya Kato, Tochigi (JP); Naoko Saito, Utsunomiya (JP); Michiaki Inoue, Cincinnati, OH (US); Kayoko Nomizu, Chuo-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/693,295

(22) Filed: Dec. 4, 2012

(65) Prior Publication Data

US 2013/0210022 A1    Aug. 15, 2013

Related U.S. Application Data

(60) Provisional application No. 61/596,967, filed on Feb. 9, 2012.

(51) Int. Cl.
*G01N 33/53* (2006.01)
*C12Q 1/02* (2006.01)
*G01N 33/566* (2006.01)

(52) U.S. Cl.
CPC .............. *C12Q 1/025* (2013.01); *G01N 33/566* (2013.01); *G01N 2500/10* (2013.01)

(58) Field of Classification Search
None
See application file for complete search history.

(56) References Cited

U.S. PATENT DOCUMENTS

| 5,272,134 | A | 12/1993 | Berliner |
| 7,344,845 | B2 | 3/2008 | Han et al. |
| 7,585,833 | B2 | 9/2009 | Fadel et al. |
| 2008/0032913 | A1 | 2/2008 | Finke et al. |
| 2013/0216492 | A1 | 8/2013 | Kato et al. |

FOREIGN PATENT DOCUMENTS

| JP | 11-241089 | 9/1999 |
| JP | A 2003-24423 | 1/2003 |
| JP | 2005-325055 | 11/2005 |
| JP | 2012-050411 | 3/2012 |
| JP | 2012-050781 | 3/2012 |
| WO | WO 2005/046632 | 5/2005 |
| WO | WO 2012/029922 | 3/2012 |

OTHER PUBLICATIONS

International Search Report dated Mar. 6, 2013 for Application No. PCT/US2012/067889.

Malnic, B., "Searching for the Ligands of Odorant Receptors", Mol Neurobiol (2007) 35:175-181.
Malnic, B. et al., "The human olfactory receptor gene family", PNAS, Feb. 24, 2004, vol. 101, No. 8, pp. 2584-2589.
International Search Report dated Sep. 7, 2012 for Application No. PCT/JP2012/064862.
Zhuang, H., et al., "Synergism of Accessory Factors in Functional Expression of Mammalian Odorant Receptors", Journal of Biological Chemistry, vol. 282, No. 20, May 1, 2007, pp. 15284-15293.
International Search Report and Written Opinion dated Feb. 13, 2014 for Application No. PCT/IB2012/003131.
Hindenland, D.M., et al., "Reducing Odiferous Volatiles with Zeolites", Cosmetics &.Toiletries, vol. 123, No. 7, Jul. 1, 2008, pp. 67-74. XP009167115.
Kawasaki, K., "Odor masking compositions containing fragrant substances for hair cosmetics", Database Caplus [Online] Chemical Abstracts Service, 2003. XP002719480.
Shimazaki, K., et al., "Alkylpyrazine-odor-blocking agents containing pyrazines", Database Caplus [Online] Chemical Abstracts Service, Jan. 28, 2003. XP002719444.
Shimazaki, K., et al., "Evaluation of the odor activity of pyrazine derivatives using structural and electronic parameters derived from conformational study by molecular mechanics (MM3) and ab initio calculations", Journal of Molecular Structure, 749 (2005), pp. 169-176.
Abstract and English Machine Translation of Japanese Application. JP 11-241089.
Abstract and English Machine Translation of Japanese Patent JP 2005-325055.
Abstract and English Machine Translation of Japanese Patent JP 2012-050411.
Abstract and English Machine Translation of Japanese Patent JP 2012-050781.
Waller, G., and Feather, M. Eds., "The Maillard Reaction in Foods and Nutrition", ACS Symposium Series vol. 215, Apr. 29, 1983, Chapter 12, pp. 185-286.

(Continued)

*Primary Examiner* — Michael Pak
(74) *Attorney, Agent, or Firm* — Frost Brown Todd LLC

(57) ABSTRACT

A method to identify an agent for reducing an odor of a pyrazine derivative, comprising:
 adding a test substance and a pyrazine derivative represented by the following Formula (I):

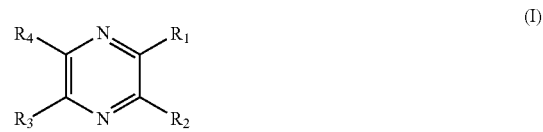

(I)

wherein $R_1$ represents methyl, ethyl, or acetyl; and $R_2$, $R_3$, and $R_4$ each independently represent hydrogen or methyl, to an olfactory receptor OR5K1 or a polypeptide having at least 80% identity to the amino acid sequence of the olfactory receptor OR5K1;
 measuring a response of the olfactory receptor to the pyrazine derivative; and
 identifying a test substance inhibiting the response of the olfactory receptor on the basis of the measured response.

9 Claims, 3 Drawing Sheets

(56) References Cited

OTHER PUBLICATIONS

English Abstract and Machine Translation for Japanese Publication No. JP A 2003-24423, Jan. 28, 2003.

Oka, Y., et al., "The identification of the sense of smell receptor antagonist and physiologic significance," A Collection of Japan Society for Bioscience, Mar. 5, 2003, col. $2003^{rd}$, pp. 152.

Oka, Y., et al., "Olfactory receptor antagonism between odorants," The EMBO Journal, 2004, vol. 23, No. 1, pp. 120-126.

Saito, H., et al., "Odor coding by a Mammalian receptor repertoire," Sci. Signal., 2009, vol. 2, No. 60, ra9, pp. 1-28.

Sanz, G., et al., "Comparison of odorant specificity of two human olfactory receptors form different phylogenetic classes and evidence for antagonism," Chem. Sense, 2005, vol. 30, No. 1, pp. 69-80.

Imahori, K, et al., "Skatole," Biochemistry dictionary, Mar. 1, 2000, The Fourth Impression of the $3^{rd}$ Ed., pp. 726-727.

Touhara, K., "Function of the sense of smell receptor—Expression and function of the olfactory receptor gene superfamily," Igaku No Ayumi, Ushiyaku Pub. Inc., Jan. 1, 2005, vol. 212, No. 1, pp. 77-81.

Abstract and English Machine Translation of Japanese Application. JP 11-241089, Sep. 9, 1999.

Abstract and English Machine Translation of Japanese Patent JP 2005-325055, Nov. 24, 2005.

Abstract and English Machine Translation of Japanese Patent JP 2012-050411, Mar. 15, 2012.

Abstract and English Machine Translation of Japanese Patent JP 2012-050781, Mar. 15, 2012.

SEQUENCE LISTING

```
<160> NUMBER OF SEQ ID NOS: 4

<210> SEQ ID NO 1
<211> LENGTH: 927
<212> TYPE: DNA
<213> ORGANISM: Homo Sapiens
<220> FEATURE:
<223> OTHER INFORMATION: OR5K1

<400> SEQUENCE: 1
atggctgaag aaaatcatac catgaaaaat gagtttatcc tcacaggatt tacagatcac    60
cctgagctga agactctgct gtttgtggtg ttctttgcca tctatctgat caccgtggtg   120
gggaatatta gtttggtggc actgatattt acacaccgtc ggcttcacac accaatgtac   180
atctttctgg gaaatctggc tcttgtggat tcttgctgtg cctgtgctat tacccccaaa   240
atgttagaga acttctttc tgagaacaaa aggatttccc tctatgaatg tgcagtacag   300
```

-continued

```
tttttattttc tttgcactgt ggaaactgca gactgctttc ttctggcagc aatggcctat      360
gaccgctatg tggccatatg caacccactg cagtaccaca tcatgatgtc caagaaactc      420
tgcattcaga tgaccacagg ggccttcata gctggaaacc tgcattccat gattcatgta      480
gggcttgtat ttaggttagt ttttcgtgga tcgaatcaca tcaaccactt ttactgtgat      540
attcttccct tgtatagact ctcttgtgtt gatccttata tcaatgaact ggttctattc      600
atcttctcag gttcagttca agtctttacc ataggtagtg tcttaatatc ttatctctat      660
attcttctta ctattttcaa aatgaaatcc aaagagggaa gggccaaagc ttttctacc       720 tgtgcatccc acttttttgtc agtttcatta ttctatggat ctcttttctt catgtacgtt      780
agaccaaatt tgcttgaaga agggggataaa gatataccag ctgcaatttt atttacaata     840
gtagttccct tactaaatcc tttcatttat agcctgagaa atagggaagt aataagtgtc      900
ttaagaaaaa ttctgatgaa gaaataa                                           927
```

<210> SEQ ID NO 2
<211> LENGTH: 308
<212> TYPE: PRT
<213> ORGANISM: Homo Sapines
<220> FEATURE:
<223> OTHER INFORMATION: OR5K1

<400> SEQUENCE: 2

```
Met Ala Glu Glu Asn His Thr Met Lys Asn Glu Phe Ile Leu Thr Gly
  1               5                  10                  15

Phe Thr Asp His Pro Glu Leu Lys Thr Leu Leu Phe Val Val Phe Phe
             20                  25                  30

Ala Ile Tyr Leu Ile Thr Val Val Gly Asn Ile Ser Leu Val Ala Leu
         35                  40                  45

Ile Phe Thr His Arg Arg Leu His Thr Pro Met Tyr Ile Phe Leu Gly
     50                  55                  60

Asn Leu Ala Leu Val Asp Ser Cys Cys Ala Cys Ala Ile Thr Pro Lys
 65                  70                  75                  80

Met Leu Glu Asn Phe Phe Ser Glu Asn Lys Arg Ile Ser Leu Tyr Glu
                 85                  90                  95

Cys Ala Val Gln Phe Tyr Phe Leu Cys Thr Val Glu Thr Ala Asp Cys
            100                 105                 110

Phe Leu Leu Ala Ala Met Ala Tyr Asp Arg Tyr Val Ala Ile Cys Asn
        115                 120                 125

Pro Leu Gln Tyr His Ile Met Met Ser Lys Lys Leu Cys Ile Gln Met
    130                 135                 140

Thr Thr Gly Ala Phe Ile Ala Gly Asn Leu His Ser Met Ile His Val
145                 150                 155                 160

Gly Leu Val Phe Arg Leu Val Phe Cys Gly Ser Asn His Ile Asn His
                165                 170                 175

Phe Tyr Cys Asp Ile Leu Pro Leu Tyr Arg Leu Ser Cys Val Asp Pro
            180                 185                 190

Tyr Ile Asn Glu Leu Val Leu Phe Ile Phe Ser Gly Ser Val Gln Val
        195                 200                 205

Phe Thr Ile Gly Ser Val Leu Ile Ser Tyr Leu Tyr Ile Leu Leu Thr
    210                 215                 220

Ile Phe Lys Met Lys Ser Lys Glu Gly Arg Ala Lys Ala Phe Ser Thr
225                 230                 235                 240

Cys Ala Ser His Phe Leu Ser Val Ser Leu Phe Tyr Gly Ser Leu Phe
                245                 250                 255
```

```
Phe Met Tyr Val Arg Pro Asn Leu Leu Glu Glu Gly Asp Lys Asp Ile
            260                 265                 270

Pro Ala Ala Ile Leu Phe Thr Ile Val Val Pro Leu Leu Asn Pro Phe
        275                 280                 285

Ile Tyr Ser Leu Arg Asn Arg Glu Val Ile Ser Val Leu Arg Lys Ile
        290                 295                 300

Leu Met Lys Lys
305

<210> SEQ ID NO 3
<211> LENGTH: 681
<212> TYPE: DNA
<213> ORGANISM: Homosapiens
<220> FEATURE:
<223> OTHER INFORMATION: RTP1S

<400> SEQUENCE: 3
atgtgcaagt ccctgacaac gggagagtgg aagaagatct tctacgagaa aatggaggag    60
gtgaaacccg cagactcctg ggacctgatc atggatccca acctccagca taacgtattg   120
gcccccggat ggaagcagta cctggagcag cacgcctctg gccgcttcca ctgctcctgg   180
tgctggcata gctggcagtc ctcccaactg gtgatcctct ccacatgta cctggataag   240 acccagcgga cgggctgcgt gcgcatgaga gtcttcaagc agctctgcta cgagtgtggc   300
tcctcccggc tggacgagtc gtccatgctg gaggagaaca tagaggggct ggtggacaac   360
ctcgtctgca gcctccggga gcagtgctac ggggagaatg ggggacagta ccgcatccac   420
gtggcctccc gccaagacca ccagcgccac cggggagagt ctgcgaggc ctgccgcctg   480 ggcatcaccc actggaagcc cacggagaag atgctagagg aggaggcctc cacctacacc   540
ttctcccggc tgcgaatcc ttccaagaca gccgactcgg gtttcagctg tgacttctgc   600
tccctccctt ggtgtatgtt ctgggccacg gtgctcttgc tcatcatata cctgcagatc   660
tccttcggca accctgtcta a                                              681

<210> SEQ ID NO 4
<211> LENGTH: 226
<212> TYPE: PRT
<213> ORGANISM: Homo Sapiens
<220> FEATURE:
<223> OTHER INFORMATION: RTP1S

<400> SEQUENCE: 4

Met Cys Lys Ser Leu Thr Thr Gly Glu Trp Lys Lys Ile Phe Tyr Glu
  1               5                  10                  15

Lys Met Glu Glu Val Lys Pro Ala Asp Ser Trp Asp Leu Ile Met Asp
             20                  25                  30

Pro Asn Leu Gln His Asn Val Leu Ala Pro Gly Trp Lys Gln Tyr Leu
         35                  40                  45

Glu Gln His Ala Ser Gly Arg Phe His Cys Ser Trp Cys Trp His Ser
     50                  55                  60

Trp Gln Ser Ser Gln Leu Val Ile Leu Phe His Met Tyr Leu Asp Lys
 65                  70                  75                  80

Thr Gln Arg Thr Gly Cys Val Arg Met Arg Val Phe Lys Gln Leu Cys
                 85                  90                  95

Tyr Glu Cys Gly Ser Ser Arg Leu Asp Glu Ser Ser Met Leu Glu Glu
            100                 105                 110

Asn Ile Glu Gly Leu Val Asp Asn Leu Val Cys Ser Leu Arg Glu Gln
        115                 120                 125
```

```
Cys Tyr Gly Glu Asn Gly Gly Gln Tyr Arg Ile His Val Ala Ser Arg
    130              135              140

Gln Asp His Gln Arg His Arg Gly Glu Phe Cys Glu Ala Cys Arg Leu
145              150              155                      160

Gly Ile Thr His Trp Lys Pro Thr Glu Lys Met Leu Glu Glu Glu Ala
                165              170                  175

Ser Thr Tyr Thr Phe Ser Arg Pro Ala Asn Pro Ser Lys Thr Ala Asp
            180              185              190

Ser Gly Phe Ser Cys Asp Phe Cys Ser Leu Pro Trp Cys Met Phe Trp
        195              200              205

Ala Thr Val Leu Leu Leu Ile Ile Tyr Leu Gln Ile Ser Phe Gly Asn
    210              215              220

Pro Val
225
```

METHOD OF IDENTIFYING AN AGENT FOR INHIBITING ODOR OF PYRAZINE DERIVATIVES

CROSS REFERENCE TO RELATED APPLICATION

This application claims priority from U.S. Provisional Patent Application No. 61/596,967 filed on Feb. 9, 2012, which is incorporated herein by reference in its entirety.

FIELD OF THE INVENTION

The present invention relates to a method to identify an agent for inhibiting an odor of a pyrazine derivative.

BACKGROUND OF THE INVENTION

There are a large number of malodorous molecules having different polarities and molecular weights in our living environment. Hitherto, a variety of methods have been developed for reducing various malodors. In general, the methods for reducing malodors are roughly classified into biological methods, chemical methods, physical methods, and sensory methods. Among malodorous molecules, short-chain fatty acids and amines, having high polarity, can be reduced by chemical methods, i.e., neutralization. Sulfur compounds such as thiol can be deodorized by physical methods, i.e., absorptive treatment. However, there still remain many malodorous molecules which cannot be reduced by known malodor reducing methods.

In addition, the known malodor reducing methods by the chemical neutralization or the absorptive treatment take long time for reducing the amounts of malodorous substances and thereby lack immediate effect. A method of reducing malodor by using an aromatic and thereby providing strong perception of another odor is also known. However, the odor of the aromatic may cause discomfort in this method. Moreover, these known methods may get rid of odors other than the target malodors. Thus, there is a demand for a malodor reducing method which can overcome these problems.

In mammals including humans, the mechanism for odorant recognition includes binding odorant molecules to olfactory receptors present on olfactory sensory neurons included in the olfactory epithelium, which is present in an upper portion of the nasal cavity, and transmitting the response of the receptors to the central nervous system. It has been reported that, 387 different olfactory receptors are present in human, and the genes encoding these olfactory receptors account for about 3% of the human genome. In general, a plurality of olfactory receptors responds to a plurality of odorant molecules. Specifically, one single olfactory receptor responds to a plurality of structurally similar odorant molecules at different affinities, while one single odorant molecule is detected by a plurality of olfactory receptors. It is also reported that a certain odorant molecule which can activate one olfactory receptor serves as an antagonist which inhibits activation of another olfactory receptor. Such combined response of these olfactory receptors leads to recognition of each odor.

Thus, when a first odorant molecule is co-present with a second odorant molecule, in some cases, the response of an olfactory receptor to the first odorant molecule is inhibited by the second odorant molecule. Through the inhibition, the odor of the first odorant molecule recognized by olfactory receptors may vary considerably. This mechanism is called "olfactory receptor antagonism." Odor modulation by olfactory receptor antagonism can inhibits recognition specific to a malodor, and therefore differs in mechanism from a malodor reducing method by adding a perfume, an aromatic, or a like substance to the target odorant. In addition, the odor of an aromatic causing an unpleasant sensation to users can be prevented. Therefore, odor modulation based on olfactory receptor antagonism is a preferred means for reducing malodor.

In order to mask a malodor with an odor of, for example, a perfume or an aromatic, it is necessary to identify an odor substance exhibiting an effective malodor reducing function on the target malodor substance. Hitherto, odors have been evaluated through a sensory test by specialists. However, the sensory test has problems. The problems include for example, odor-evaluators must be trained, and the throughput of the test is low. Thus, identification of an odor substance exhibiting a malodor reducing function is not easy.

A skin tanning agent (also called a self-tanning agent or a sunless tanning agent) is a skin cosmetic for staining the skin. As a component for providing skin with a brown color, dihydroxyacetone (DHA) is mainly used alone or together with, for example, erythrulose. These components react with the upper layer of the skin to change the color of skin to brown. This staining probably progresses by a browning reaction, but the details of the reaction mechanism have been hardly clarified. The browning reaction is also called a Maillard reaction in the food chemistry field and is a term referring to a reaction for generating a brown polymer called melanoidin by polymerizing a nitrogen-containing compound, such as an amino acid or a protein, and a reducing sugar. The Maillard reaction is caused by, for example, heating of a food and is involved in coloring of the food and generation of a flavor component.

Pyrazines are known to be generated by the Maillard reaction and as a component of a roasted aroma of a food. Patent Document 1 describes an odor-blocking agent including a functional pyrazine compound as an active ingredient for blocking the odor of an alkylpyrazine compound. Pyrazines are usually used as flavoring agents for foods, and the odors of pyrazines are rather utilized. In the food field, odors obtained by the Maillard reaction are reported in Non-Patent Document 1. In Non-Patent Document 1, the pyrazine compound is described as a preferred odor which characterizes a food. For example, 2,6-dimethylpyrazine is described as having a "sweet, fried, resembling fried potatoes, nutty, roasted" odor.

PRIOR ART

Patent Document

[Patent Document 1] JP-A-2003-024423

Non-Patent Document

[Non-Patent Document 1] S. Fors, Sensory Properties of Volatile Maillard Reaction Products and Related Compounds, "The Maillard Reaction in Foods and Nutrition" (ACS Symposium Series, Vol. 215), Chapter 12, pp. 185-286 Publication Date (Print): Apr. 29, 1983

SUMMARY OF THE INVENTION

The present invention provides a method to identify an agent for reducing an odor of a pyrazine derivative, including:

adding a test substance and a pyrazine derivative represented by the following Formula (I):

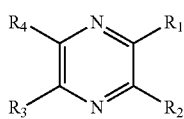

wherein R₁ represents methyl, ethyl, or acetyl; and R₂, R₃, and R₄ each independently represent hydrogen or methyl, to olfactory receptor OR5K1 or a polypeptide having at least 80% identity to the amino acid sequence of the olfactory receptor OR5K1;

measuring a response of the olfactory receptor to the pyrazine derivative; and identifying a test substance inhibiting the response of the olfactory receptor on the basis of the measured response.

DETAILED DESCRIPTION OF THE INVENTION

Figure 1:
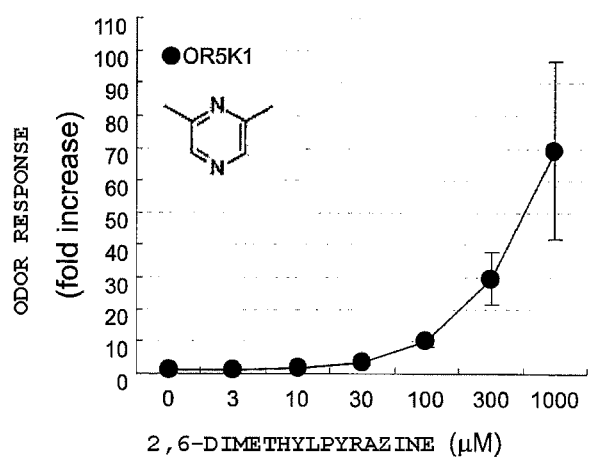
FIG. 1 shows responses of olfactory receptor OR5K1 to various concentrations of 2,6-dimethylpyrazine, wherein n=5 and error bar=±SE.

A problem that the use of a commercially available skin tanning agent (self-tanning agent or sunless tanning agent) involves a characteristic unpleasant odor expressed as, for example, an earthy or burnt sugar odor has been reported (D. M. Hindenlang and M. E. McDonnell, Cosmetics & Toiletries magazine, 2008, Vol. 123, No. 7, pp. 67-74), and there has been a demand for improvement thereof. The cause of the unpleasant odor has been investigated to reveal that dimethylpyrazine, which is generated when dihydroxyacetone (DHA) or erythrulose in a skin tanning agent reacts with the skin to change the color of skin to brown, is one of causative substances. Furthermore, it has been revealed that, in addition to dimethylpyrazine, other pyrazine derivatives yield similar odors, and there is a demand for reducing the odor of these pyrazine derivatives.

In order to attain the olfactory receptor antagonism, an olfactory receptor which responds to a target malodorous substance must be determined, and substance which effectively exhibits an antagonistic effect on an olfactory receptor of malodorous substance must be searched and identified. Accordingly, the present inventors have searched for an olfactory receptor which responds to a pyrazine derivative and have succeeded in identification of the receptor. Furthermore, the present inventors have found that the substance which inhibits response of the olfactory receptor can reduce the odor of the pyrazine derivative through masking by the olfactory receptor antagonism.

According to the present invention, an agent for reducing the odor of a pyrazine derivative can be efficiently identified. According to an inhibitor identified by the present invention, the odor of a pyrazine derivative, for example, the odor generated by using a known self-tanning agent (or sunless tanning agent) can be specifically reduced without causing problems which occur in known malodor reducing methods using a deodorant or an aromatic, such as lack of immediate effect and discomfort due to an odor of an aromatic.

As used herein, the term "masking" in the odor-related field generally refers to means for reducing or weakening recognition of a target odor. The term "masking" may encompass chemical means, physical means, biological means, and sensory means. Examples of the masking means include any means for removing an odorant molecule responsible for a target odor from the environment (e.g., adsorption and chemical decomposition of the odorant); means for preventing release of a target odor to the environment (e.g., sealing); and a method in which recognition of a target odor is reduced by adding another odorant such as a flavoring agent or an aromatic.

As used herein, the term "masking through olfactory receptor antagonism" refers to one embodiment of the aforementioned broadly defined "masking" and is means for inhibiting the response of an olfactory receptor to a target odorant molecule by an additional odorant molecule, to thereby modulate the odor of the target odorant molecule recognized by a subject. Although masking through olfactory receptor antagonism employs an additional odorant molecule, the masking differs from means for canceling out a target odor by use of a strong odorant such as a perfume. In one embodiment of masking through olfactory receptor antagonism, a substance which can inhibit the response of an olfactory receptor such as an antagonist is used. When a response-inhibiting substance which can specifically inhibit the response of a receptor related to recognition of a certain odor is employed, the response of the receptor is suppressed, whereby the odor recognized by a subject can be modulated.

"Pyrazine derivatives" in the present invention are compounds represented by the following Formula (I):

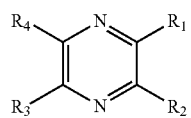

In Formula (I), R₁ represents methyl, ethyl, or acetyl; and R₂, R₃, and R₄ each independently represent hydrogen or methyl. At least one of R₁ to R₄ is preferably an alkyl group. Examples of the pyrazine represented by Formula (I) of the present invention include 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2-ethyl-6-methylpyrazine, 3-methyl-2-acetylpyrazine, and 3,5-dimethyl-2-acetylpyrazine.

In the present invention, the "odor of a pyrazine derivative" can be an odor due to a pyrazine derivative represented by Formula (I). The "odor of a pyrazine derivative" in the present invention can be an odor generated by a Maillard reaction and is typically described as a roasted odor and the like. For example, Non-Patent Document 1 describes that 2,6-dimethylpyrazine has a "sweet, fried, resembling fried potatoes, nutty, roasted" odor. In addition, the "odor of a pyrazine derivative" in the present invention can be expressed as an odor generated when a known self-tanning agent is applied to skin, more specifically, an earthy odor or an odor generated when dihydroxyacetone (DHA) or erythrulose reacts with the skin to change the color of skin to brown.

The present inventors identified olfactory receptor OR5K1 from many olfactory receptors as a sole receptor which responds to pyrazine derivatives. The response of OR5K1 to pyrazine derivatives has not been found until now, and OR5K1 is a novel receptor for the pyrazine derivatives.

Figure 2:
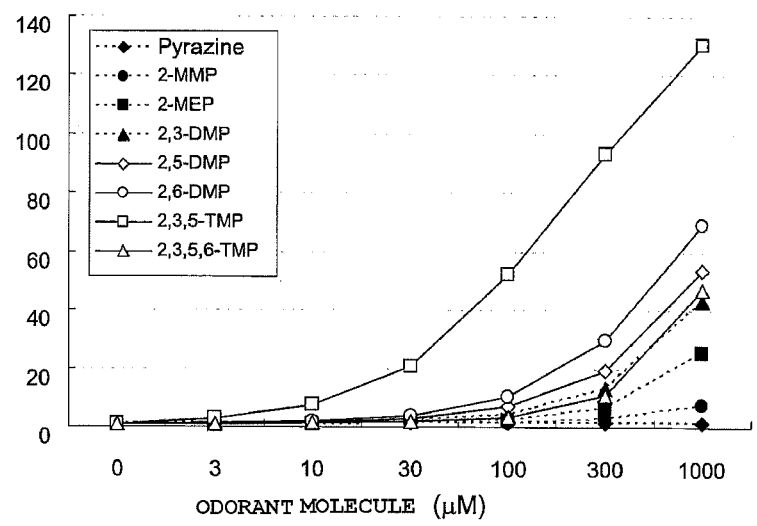
FIG. 2 shows responses of olfactory receptor OR5K1 to various concentrations of pyrazine derivatives, wherein n=3 to 5 and error bar=±SE.

As shown in FIGS. 1 and 2, OR5K1 responds to pyrazine derivatives represented by Formula (I) in dose-dependent manner. Consequently, a substance which inhibits the response of OR5K1 causes a change in perception of odors of pyrazine derivatives in the central nervous system by masking based on the olfactory receptor antagonism and, as a result, can reduce the odor in an odor-specific manner.

Accordingly, an aspect of the present invention provides a method to identify an agent for reducing an odor of a pyrazine derivative. The method includes the steps of adding a test substance and a pyrazine derivative represented by Formula (I) to olfactory receptor OR5K1; measuring response of the olfactory receptor to the pyrazine derivative; and identifying a test substance inhibiting the response of the olfactory receptor on the basis of the measured response. The identified test substance is selected as the agent for reducing an odor of a pyrazine derivative. The method of the present invention can be performed in vitro or ex vivo.

In the method of the present invention, a test substance and a pyrazine derivative serving as a causative substance for an odor are added to olfactory receptor OR5K1. The pyrazine derivative used in the method of the present invention may be any pyrazine derivative represented by Formula (I). In the pyrazine derivative represented by Formula (I) used in the method of the present invention, at least one of $R_1$ to $R_4$ is preferably an alkyl group.

Preferred examples of the pyrazine derivative used in the method of the present invention include 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2-ethyl-6-methylpyrazine, 3-methyl-2-acetylpyrazine, and 3,5-dimethyl-2-acetylpyrazine.

Among them, 2-monomethylpyrazine, 2-monoethylpyrazine, 2,3-dimethylpyrazine, 2,5-dimethylpyrazine, 2,6-dimethylpyrazine, 2,3,5-trimethylpyrazine, and 2,3,5,6-tetramethylpyrazine are more preferred; and 2,3-dimethylpyrazine, 2,5-dimethylpyrazine, 2,6-dimethylpyrazine, 2,3,5-trimethylpyrazine, and 2,3,5,6-tetramethylpyrazine are even more preferred.

The test substance used in the method of the present invention may be any material which is desired to be used as an agent for reducing an odor of a pyrazine derivative. The test substance may be a natural material or may be artificially synthesized by a chemical or biological method and may be a compound, a composition, or a mixture thereof.

Olfactory receptor OR5K1 used in the method of the present invention is expressed in human olfactory cells and has been registered in GenBank under the accession number GI: 115270955. OR5K1 is a protein encoded by a gene having a nucleotide sequence represented by SEQ ID NO: 1 and having the amino acid sequence represented by SEQ ID NO: 2.

In the method of the present invention, the olfactory receptor can be used in any form that does not lose the responsiveness to a pyrazine derivative. For example, the olfactory receptor can be used in a form of a tissue, a cell, or a culture which naturally expresses the olfactory receptor, such as an olfactory organ or olfactory cells isolated from a living body; membrane of olfactory cells carrying the olfactory receptor; a recombinant cell genetically engineered to express the olfactory receptor or a culture of the cell; membrane of the recombinant cells; or artificial lipid bilayer membrane having the olfactory receptor. These forms are included in the range of the olfactory receptor used in the present invention.

In a preferred embodiment, cells, such as olfactory cells, naturally expressing the olfactory receptor, genetically engineered recombinant cells expressing the olfactory receptor, or a culture of such cells can be used. The recombinant cells can be produced by transforming cells with a vector carrying a gene encoding the olfactory receptor. On this occasion, RTP1S is preferably transfected together with the receptor in order to enhance expression of the olfactory receptor in cell membrane.

Examples of the RTP1S which can be used in the production of the recombinant cells include human RTP1S. Human RTP1S has been registered in GenBank under the accession number GI: 50234917. Alternatively, a polypeptide having an amino acid sequence which has at least 80%, preferably at least 85%, more preferably at least 90%, more preferably at least 95%, and more preferably at least 98% identity to human RTP1S and, like human RTP1S, enhancing expression of the olfactory receptor in membrane may be used instead of human RTP1S. For example, an RTP1S variant used in Examples described in this specification is a protein encoded by a gene having a nucleotide sequence represented by SEQ ID NO: 3 and having the amino acid sequence represented by SEQ ID NO: 4. The protein has an amino acid sequence having 78.9% identity to human RTP1S, enhances expression of the olfactory receptor in membrane, and can be used in production of the recombinant cells. Alternatively, mouse RTP1S (see Sci. Signal., 2009, 2(60): rag mentioned above) is also a protein which has an amino acid sequence having 89% identity to human RTP1S, enhances expression of the olfactory receptor in membrane, and can be used in production of the recombinant cells.

In this specification, the sequence identity in nucleotide sequence or amino acid sequence is calculated by a Lipman-Pearson method (Science, 227, 1435, (1985)). Specifically, the sequence identity is calculated by analysis using a homology analysis (Search homology) program in gene information processing software Genetyx-Win (Ver. 5.1.1; Software Development Co., Ltd.) and setting Unit size to compare (ktup) to 2.

According to the present invention, after addition of a test substance and a pyrazine derivative, the response of olfactory receptor OR5K1 to the pyrazine derivative is measured. The response of the olfactory receptor may be measured by any method which is known in the art, such as measurement of intracellular cAMP levels or reporter gene assay. For example, it is known that the olfactory receptor activated by an odorant molecule couples with intracellular Gas to activate adenylate cyclase and thereby increases the amount of intracellular cAMP (Mombaerts P., Nat. Neurosci., 5, pp. 263-278). Accordingly, the intracellular cAMP amount after the addition of the odorant molecules can be used as an index for measurement of response of the olfactory receptor. The cAMP amount can be measured by, for example, ELISA or calcium imaging method.

Subsequently, the inhibition effect of a test substance on the response to the pyrazine derivative is evaluated based on the measured response of the olfactory receptor, and thereby a test substance inhibiting the response is identified. The inhibition effect can be evaluated by, for example, comparison of the measured responses of the olfactory receptor to the pyrazine derivative under addition of different concentrations of a test substance. More specifically, the response of the olfactory receptor to the pyrazine derivative is compared between a group of high concentration test substance and a group of low concentration test substance; between a group containing a test substance and a group not containing the test substance; or between before and after addition of a test substance. If the response of the olfactory receptor is inhibited by addition of a test substance or by addition of a higher concentration of a test substance, the test substance can be identified as a material which inhibits response of the olfactory receptor to the pyrazine derivative.

In the method of the present invention, a polypeptide having a function equivalent to OR5K1 can be used as an olfactory receptor instead of OR5K1. Examples of the polypeptide include polypeptides composed of amino acid sequences having at least 80%, preferably at least 85%, more preferably at least 90%, more preferably at least 95%, and more preferably at least 98% identity to the amino acid sequence (SEQ ID NO: 2) of OR5K1 and having responsiveness to the pyrazine derivative.

In the method of the present invention, the above-described OR5K1 and the polypeptides having a function equivalent to that of OR5K1 may be used alone or in a combination of two or more thereof as the olfactory receptor.

The test substance identified by the above-described procedure is a substance which inhibits response of the olfactory receptor to a pyrazine derivative and thereby causes a change in perception of the odor of the pyrazine derivative in the central nervous system by masking based on the olfactory receptor antagonism. As a result, the test substance can reduce the level of human perception of the odor of the pyrazine derivative. Consequently, the test substance identified by the above-described procedure is selected as an agent for reducing the odor of the pyrazine derivative.

For example, if the response of the receptor in a group containing a test substance in the above-described measurement procedure is reduced to 60% or less, preferably 50% or less, or more preferably 25% or less of the response in a control group, the test substance can be selected as an agent for reducing the odor of the pyrazine derivative.

The substance selected by the method of the present invention can reduce an odor of a pyrazine derivative by olfactory masking based on inhibition of response of the olfactory receptor to the odor of the pyrazine derivative. Consequently, the substance can be used as an active ingredient for reducing an odor of a pyrazine derivative, for example, a roasted odor, an odor generated by a Maillard reaction, an odor generated when a self-tanning agent is applied to the skin (e.g., earthy odor), or an odor generated when DHA or erythrulose reacts with the skin to change the color of skin to brown.

For example, the substance selected by the method of the present invention can be an active ingredient of an agent for reducing an odor of a pyrazine derivative. Alternatively, the substance selected by the method of the present invention can be contained in compounds or compositions for reducing the odor of pyrazine derivatives as active ingredients for reducing the odor of the pyrazine derivatives. Alternatively, the antagonists can be used for producing agents for reducing the odor of pyrazine derivatives or for producing compounds or compositions for reducing the odor of pyrazine derivatives.

For example, the substance selected by the method of the present invention can be used as active ingredients for reducing the odor of pyrazine derivatives in every compound or composition desired to reduce the odor of the pyrazine derivatives or under every environment desired to reduce the odor of the pyrazine derivatives. Alternatively, the substance selected by the method of the present invention can be used for producing compounds or compositions desired to reduce the odor of pyrazine derivatives as active ingredients for reducing the odor of the pyrazine derivatives. Examples of the compounds or the compositions desired to reduce the odor of the pyrazine derivatives include skin tanning agents (also called self-tanning agent or sunless tanning agent), for example, a skin tanning agent containing dihydroxyacetone (DHA) or erythrulose as a color former and another skin tanning agent utilizing a browning reaction. The pyrazine derivatives may be contained in foods as flavoring components and may cause off-flavors if their amounts are high. Accordingly, other examples of the compounds or the compositions desired to reduce the odor of the pyrazine derivatives include foods containing the pyrazine derivatives as flavoring components and compositions thereof, more specifically, foods, such as roasted peanuts and milk powders, of which taste is reduced by the presence of excess amounts of pyrazine derivatives and compositions thereof.

EXAMPLES

The present invention will now be described more specifically by examples.

Example 1

Identification of Olfactory Receptor Responding to Pyrazine Derivative

1) Cloning of Human Olfactory Receptor Gene

Human olfactory receptors were cloned based on sequence information registered in GenBank by PCR using human genomic DNA female (G1521: Promega Corporation) as a template. Each gene amplified by PCR was inserted into a pENTR vector (Invitrogen Inc.) in accordance with the manual and was recombined into the NotI and AscI site located downstream of a Flag-Rho tag sequence in a pME18S vector using the NotI and AscI site present in the pENTR vector.

2) Production of pME18S-RTP1S Vector

An RTP1S variant gene (SEQ ID NO: 3) encoding an RTP1S variant (SEQ ID NO: 4) was inserted into the EcoRI and XhoI site of a pME18S vector.

3) Production of Olfactory Receptor-Expressing Cell

HEK293 cells expressing 373 types of human olfactory receptors were produced. A reaction solution having a composition shown in Table 1 was prepared and left to stand in a clean bench for 15 min and then was dispensed in each well of a 96-well plate (Becton, Dickinson and Company). Subsequently, HEK293 cells (100 µL, $3\times10^5$ cells/cm$^2$) were seeded in each well and cultured in an incubator at 37° C. and 5% $CO_2$ for 24 hr.

TABLE 1

| | |
|---|---:|
| OPTI-MEM (GIBCO) | 50 µL |
| Human olfactory receptor gene (incorporated in a pME18S vector having a Flag-Rho tag at the N-terminal) | 0.075 µg |
| pGL4.29 (fluc2P-CRE-hygro, Promega Corp.) | 0.03 µg |
| pGL4.75 (hRluc-CMV, Promega Corp.) | 0.03 µg |
| pME18S-RTP1S variant vector | 0.03 µg |
| Lipofectamine 2000 (Invitrogen Inc.) | 0.4 µl |

4) Luciferase Assay

An olfactory receptor expressed in HEK293 cells couples with endogenous Gas in the cells to activate adenylate cyclase and thereby increases the amount of intracellular cAMP. In this study, the response of a pyrazine derivative was measured by luciferase reporter gene assay which monitors an increase in the amount of intracellular cAMP as the luminescence value derived from a firefly luciferase gene (fluc2P-CRE-hygro). A Renilla luciferase gene was fused downstream of a CMV promoter (hRluc-CMV) and was also introduced to HEK293 cells as an internal standard to correct errors in transgenic efficiency and number of cells.

The culture medium was removed from the culture produced in the above 3), and 75 μL of a solution prepared with a CD293 medium (Invitrogen Inc.) so as to contain a pyrazine derivative (1 mM 2,6-dimethylpyrazine) was added thereto. The cells were cultured in a $CO_2$ incubator for 2.5 hr to sufficiently express the luciferase gene in the cells. The luciferase activity was measured with a Dual-Glo™ luciferase assay system (Promega Corporation) in accordance with the operating manual of the system. The fold increases were calculated by dividing the luminescence value derived from firefly luciferase induced by stimulation with a pyrazine derivative at each concentration by the luminescence value in cells not stimulated with the pyrazine derivative and were used as an index of response strength.

5) Results

The response of each of the 373 types of olfactory receptors to 2,6-dimethylpyrazine (1 mM) was measured, and the result showed that only olfactory receptor OR5K1 responded to 2,6-dimethylpyrazine (FIG. 1). Response of OR5K1 to 2,6-dimethylpyrazine has not been reported until now, and therefore OR5K1 is a novel 2,6-dimethylpyrazine receptor.

Example 2

Response Characteristics of OR5K1 to Pyrazine Derivatives

Olfactory receptor OR5K1 (SEQ ID NO: 2) was expressed in HEK293 cells together with an RTP1S variant (SEQ ID NO: 4) by the same procedure as in Example 1, and the dependency of the response on the concentration (0, 3, 10, 30, 100, 300, and 1000 μM) of various pyrazine compounds was investigated. The pyrazine compounds used in this Example were pyrazine and pyrazine derivatives selected from the group consisting of 2-methylpyrazine, 2,3-dimethylpyrazine, 2,5-dimethylpyrazine, 2,3,5-trimethylpyrazine, 2,3,5,6-tetramethylpyrazine and 2-ethylpyrazine.

The results showed that OR5K1 responded in a dose-dependent manner to the pyrazine derivatives, i.e., 2-methylpyrazine (2-MMP), 2,3-dimethylpyrazine (2,3-DMP), 2,5-dimethylpyrazine (2,5-DMP), 2,6-dimethylpyrazine (2,6-DMP), 2,3,5-trimethylpyrazine (2,3,5-TMP), 2,3,5,6-tetramethylpyrazine (2,3,5,6-TMP), and 2-ethylpyrazine (2-MEP), but did not respond to pyrazine (FIG. 2).

Example 3

Identification of Antagonist of OR5K1

Antagonistic activities of 174 test substances against olfactory receptor OR5K1 were investigated by examining response of OR5K1 to a pyrazine derivative.

2,6-Dimethylpyrazine (1 mM) and a test substance (300 μM) shown in Table 2 were added to HEK293 cells expressing olfactory receptor OR5K1 by the same procedure as in Example 2, and the response of the olfactory receptor to 2,6-dimethylpyrazine was measured to evaluate a change in response of the receptor due to addition of the test substance. Flavoring agents recognized to have cytotoxicity were re-evaluated using a mixture of 333 μM of 2,6-dimethylpyrazine and 100 μM of a test substance.

The receptor response-inhibiting rate of a test substance was calculated as follows. The receptor activity (X−Y) by stimulation with 2,6-dimethylpyrazine alone was determined by subtracting the luminescence value (Y) in cells to which the receptor was introduced but were not stimulated with 2,6-dimethylpyrazine from the luminescence value (X) derived from firefly luciferase induced by stimulation with 2,6-dimethylpyrazine alone. Similarly, the receptor activity (Z−Y) in the presence of a test substance was determined by subtracting the luminescence value (Y) in cells not stimulated with 2,6-dimethylpyrazine from the luminescence value (Z) stimulated with a mixture of 2,6-dimethylpyrazine and the test substance. The reduction rate of the receptor activity (Z−Y) in the presence of a test substance to the receptor activity (X−Y) by stimulation with 2,6-dimethylpyrazine alone was calculated by the following computation expression:

Inhibition rate (%)={1−(Z−Y)/(X−Y)}×100, to determine the receptor response-inhibiting rate of the test substance. In the measurement, multiple independent experiments were performed in duplicate, and the average of each experiment was used.

As shown in Table 2, the results showed that 56 test substances had antagonistic activity on the response of OR5K1 to 2,6-dimethylpyrazine.

TABLE 2

| Inhibition rate: 75% or more (exceptionally strong antagonist) | Inhibition rate: 50% or more (strong antagonist) | Inhibition rate: 40% or more (weak antagonist) |
|---|---|---|
| 2-ethyl-4-(2,2,3-trimethyl-3-cyclopenten-1-yl)-2-buten-1-ol (bacdanol) | 2-methoxy-1-(phenylmethoxy)-4-(1-propenyl)-benzene (benzyl isoeugenol) | cyclo-pentadecanolide (pentalide) |
| 5-methyl-2-(1-methylethyl)-phenol (thymol) | α-methyl-β-(p-tert-butylphenyl)-propionaldehyde (lilial) | 1-(2,6,6-trimethyl-1,3-cyclohexadien-1-yl)-2-buten-1-one (damascenone) |
| 3,7-dimethyl-2,6-octadienal (citral) | l(−)-menthol | 2,4-dimethyl-3-cyclohexene-1-carboxyaldehyde (triplal) |
| phenylethyl salicylate | ω-6-hexadecenelactone (ambrettolide) | isocyclocitral |
| 1-(5,6,7,8-tetrahydro-3,5,5,6,8,8-hexamethyl-2-naphthalenyl)-ethanone (Tonalid (registered trademark), tentarome) | 2-(2-(4-methyl)-3-cyclohexen-1-yl)-propyl-cyclopentanone (nectaryl) | 6,10-dimethyl-3-oxa-9-undecenal (citronellyloxy-acetaldehyde) |
| isolongifolanone | formaldehyde cyclododecyl-ethyl acetal (Boisambrene Forte (registered trademark)) | dimethyl benzyl carbinyl acetate |
| 4-(2,6,6-trimethyl-2-cyclohexen-1-yl)-3-buten-2-one (α-ionone) | 1-(2,3,4,7,8,8a-hexahydro-3,6,8,8-tetramethyl-1H-3a,7-methanoazulen-5-yl)-ethanone (acetyl cedrene) | ethyl-(3aα,4α,7α,3aα)-octahydro-4,7-methano-3aH-indene-3a-carboxylate (Fruitate (registered trademark)) |
| 4-(2,6,6-trimethyl-1-cyclohexen-1-yl)-3-buten-2-one (β-ionone) | β-methyl naphthyl ketone | 2-pentyl-3-methyl-2-cyclopenten-1-one (dihydrojasmon) |
| vetiverol | cedryl acetate | phenylhexanol |
| 7-acetyl-1,2,3,4,5,6,7,8-octahydro-1,1,6,7-tetramethyl-naphthalene (Iso E Super) | (5E)-3-methylcyclopenta-5-decen-1-one (δ-muscenone) | 1-(5,5-dimethyl-1-cyclohexen-1-yl)-4-penten-1-one (Dynascone (registered trademark)) |
| α-amylcinnamic aldehyde | cinnamaldehyde | 6-tert-butyl-1,1-dimethylinden-4-yl methyl ketone (celestolide) |
| α-methyl-4-(1-methylethyl)-benzenepropanol (cyclamen aldehyde) | 4-(1-ethoxyvinyl)-3,3,5,5-tetramethyl cyclohexanone (kephalis) | cis-4-isopropyl-cyclohexylmethanol (mayol) |
| | α-hexylcinnamic | 1-allyl-3-methoxy- |

TABLE 2-continued

| Inhibition rate: 75% or more (exceptionally strong antagonist) | Inhibition rate: 50% or more (strong antagonist) | Inhibition rate: 40% or more (weak antagonist) |
|---|---|---|
| 4-methyl-3-decen-5-ol (undecavertol) 1-(2-tert-butyl-cyclohexyloxy)-2-butanol (Amber Core (registered trademark)) | aldehyde 2-phenyl-propionaldehyde (hydratropic aldehyde) 3,7-dimethyl-6-octenal (citronellal) dodecahydro-3a,6,6,9a-tetramethyl-naphtho[2,1-b]furan (Ambrotech (registered trademark)) 4,7,7-trimethyl-spirobicyclo[2.2.1] heptane-2,1-cyclopentan-3-one (Sagetone (registered trademark) V) α-isomethyl ionone (γ-methyl ionone) 3,7-dimethyl-1-octanol (tetra-hydrogeraniol) cedryl methyl ether muscone 2-methyl-4-(2,2,3-trimethyl-3-cyclopenten-1-yl)-2-buten-1-ol (Sandalmysore Core (registered trademark)) 2-cyclohexylpropanal (Pollenal (registered trademark) II) γ-undecalactone | 4-hydroxybenzene (eugenol) (E)-3,7-dimethyl-2,6-octadien-1-ol (geraniol) 4-tert-butyl-2,6-dimethyl-3,5-dinitro-acetophenone (musk ketone) 1,4-dioxacyclo-heptadecane-5,17-dione (ethylene brassylate) hexyl salicylate α-methyl-3,4-methylenedioxy-hydrocinnamic aldehyde (helional) |

Example 4

Evaluation of Ability of Antagonist of OR5K1 for Reducing the Odor of Pyrazine Derivatives The ability to reduce an odor of a pyrazine derivative by the antagonist materials identified in Example 3 was confirmed by a sensory test.

A flavoring agent (0.5 μL) was added to dough (0.5 g) containing 2,6-dimethylpyrazine (1%, and the odor thereof was evaluated by comparing the strength of odor of 2,6-dimethylpyrazine in dough not applied with flavor by the flavoring agent. The sensory evaluation test was performed by four panelists. In the evaluation, a case where a strong odor of 2,6-dimethylpyrazine was smelled was rated as 1, and a case where the odor of 2,6-dimethylpyrazine was not smelled at all was rated as 5.

Figure 3:
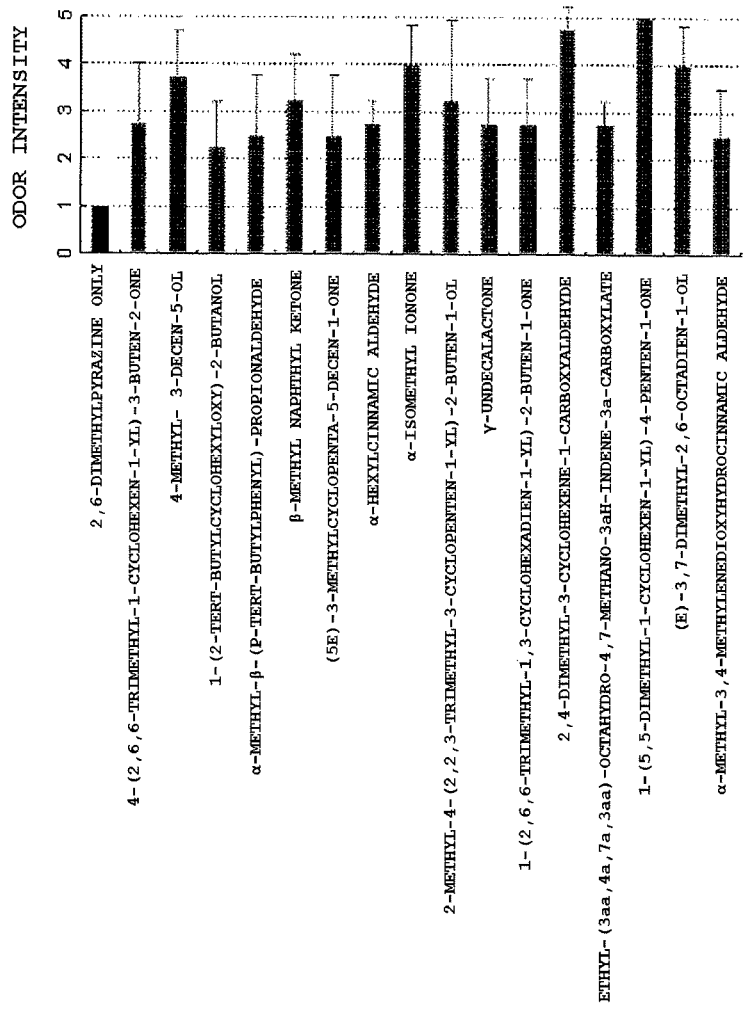
FIG. 3 shows effects of various compounds for reducing an odor of 2,6-dimethylpyrazine, wherein error bar=±SE.

As a result, the odor of 2,6-dimethylpyrazine was inhibited by the antagonists which were revealed in Example 3 to inhibit the response of OR5K1 to 2,6-dimethylpyrazine, that is, the odor of 2,6-dimethylpyrazine was inhibited by 4-(2,6,6-trimethyl-1-cyclohexen-1-yl)-3-buten-2-one (β-ionone), 4-methyl-3-decen-5-ol (undecavertol), 1-(2-tert-butylcyclohexyloxy)-2-butanol (Amber Core (registered trademark)), α-methyl-β-(p-tert-butylphenyl)-propionaldehyde (lilial), β-methyl naphthyl ketone, (5E)-3-methylcyclopenta-5-decen-1-one (δ-muscenone), α-hexylcinnamic aldehyde, α-isomethyl ionone (γ-methyl ionone), 2-methyl-4-(2,2,3-trimethyl-3-cyclopenten-1-yl)-2-buten-1-ol (Sandalmysore Core (registered trademark)), γ-undecalactone, 1-(2,6,6-trimethyl-1,3-cyclohexadien-1-yl)-2-buten-1-one (damascenone), 2,4-dimethyl-3-cyclohexene-1-carboxyaldehyde (triplal), ethyl-(3aα,4α,7α,3aα)-octahydro-4,7-methano-3aH-indene-3a-carboxylate (Fruitate (registered trademark)), 1-(5,5-dimethyl-1-cyclohexen-1-yl)-4-penten-1-one (Dynascone (registered trademark)), (E)-3,7-dimethyl-2,6-octadien-1-ol (geraniol), and α-methyl-3,4-methylenedioxy-hydrocinnamic aldehyde (helional) (FIG. 3).

The embodiments of the present invention have been described above, but it should be understood that the specific embodiments described above are not intended to limit the present invention. Various other changes and modifications within the scope of the present invention are obvious to those skilled in the art.

The literatures and patent applications cited in this specification are incorporated by reference herein in their entirety.

The invention claimed is:

1. A method to identify an agent for reducing an odor of a pyrazine derivative, comprising:
adding a test substance and a pyrazine derivative represented by the following Formula (I):

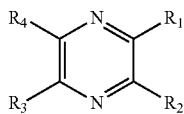

(I)

wherein $R_1$ represents methyl, ethyl, or acetyl; and $R_2$, $R_3$, and $R_4$ each independently represent hydrogen or methyl, to a recombinant cell genetically engineered to express an olfactory receptor OR5K1 or a polypeptide which maintains responsiveness to a pyrazine derivative and which has at least 90% identity to the amino acid sequence of SEQ ID NO:2, in a cultured cell;
measuring a response of the olfactory receptor to the pyrazine derivative; and
by comparing the response of the olfactory receptor or the polypeptide in the presence of the test substance to the response of the olfactory receptor or the polypeptide to the pyrazine derivative in the absence of the test substance, thereby identifying a test substance inhibiting the response of the olfactory receptor or the polypeptides on the basis of the measured response.

2. The method according to claim 1, wherein at least one of $R_1$ to $R_4$ represents an alkyl group.

3. The method according to claim 1, wherein the pyrazine derivative is selected from the group consisting of 2,6-dimethylpyrazine, 2,5-dimethylpyrazine, 2,3-dimethylpyrazine, 2,3,5-trimethylpyrazine, 2,3,5,6-tetramethylpyrazine, 2-monomethylpyrazine, 2-monoethylpyrazine, 2 ethyl-6-methylpyrazine, 3-methyl-2-acetylpyrazine, and 3,5-dimethyl-2-acetylpyrazine.

4. The method according to claim 1, wherein the olfactory receptor OR5K1 is a protein consisting of an amino acid sequence set forth in SEQ ID NO: 2.

5. The method according to claim 1, wherein the polypeptide having at least 90% identity to the amino acid sequence of SEQ ID NO: 2 is a polypeptide consisting of an amino acid sequence having at least 95% identity to the amino acid sequence set forth in SEQ ID NO: 2 and having responsiveness to the pyrazine derivative.

6. The method according to claim 1, further comprising:
measuring the response of the olfactory receptor or the polypeptide in the absence of the test substance.

7. The method according to claim 6, wherein, when the response of the olfactory receptor or the polypeptide in the presence of a test substance is reduced to 60% or less of the response of the olfactory receptor or the polypeptide in the absence of the test substance, the test substance is identified as a substance which inhibits response of the olfactory receptor or the polypeptide to the pyrazine derivative.

8. The method according to claim 1, wherein the step of measuring a response of the olfactory receptor or the polypeptide is performed using measurement of intracellular cAMP level by ELISA or calcium imaging or reporter gene assay.

9. The method according to claim 1, wherein the odor of the pyrazine derivative is an odor generated by reaction of a skin tanning agent with skin.

* * * * *